US007998470B2

(12) United States Patent
Ranganathan

(10) Patent No.: US 7,998,470 B2
(45) Date of Patent: Aug. 16, 2011

(54) COMPOSITIONS AND METHODS IMPROVING RENAL FUNCTION

(75) Inventor: Natarajan Ranganathan, Broomall, PA (US)

(73) Assignee: Kibow Biotech, Inc., Newtown, Square, PA (US)

( * ) Notice: Subject to any disclaimer, the term of this patent is extended or adjusted under 35 U.S.C. 154(b) by 190 days.

(21) Appl. No.: 11/279,159

(22) Filed: Apr. 10, 2006

(65) Prior Publication Data

US 2006/0257375 A1 Nov. 16, 2006

Related U.S. Application Data

(63) Continuation-in-part of application No. 10/803,211, filed on Mar. 18, 2004, now abandoned, which is a continuation-in-part of application No. 10/689,359, filed on Oct. 20, 2003, which is a continuation-in-part of application No. 09/855,346, filed on May 15, 2001, now Pat. No. 6,706,287, which is a continuation-in-part of application No. 09/557,011, filed on Apr. 20, 2000, now Pat. No. 6,706,263, application No. 11/279,159, which is a continuation-in-part of application No. 10/676,622, filed on Sep. 30, 2003, now Pat. No. 7,026,160, and a continuation-in-part of application No. 10/676,558, filed on Sep. 30, 2003, which is a continuation-in-part of application No. 09/855,346, which is a continuation-in-part of application No. 09/557,011.

(60) Provisional application No. 60/131,774, filed on Apr. 30, 1999.

(51) Int. Cl.
*A61K 9/50* (2006.01)

(52) U.S. Cl. .................................... 424/93.1; 424/93.44

(58) Field of Classification Search ................. 424/93.1, 424/93.44
See application file for complete search history.

(56) References Cited

U.S. PATENT DOCUMENTS

| | | | | |
|---|---|---|---|---|
| 4,022,883 | A | | 5/1977 | Setala .............................. 424/93 |
| 4,218,541 | A | | 8/1980 | Ackerman ...................... 435/262 |
| 4,427,701 | A | | 1/1984 | Morley ............................ 426/36 |
| 4,970,153 | A | | 11/1990 | Kobashi et al. ............... 435/128 |
| 5,032,399 | A | | 7/1991 | Gorbach et al. ................. 424/93 |
| 5,116,737 | A | | 5/1992 | McCoy ........................... 435/42 |
| 5,145,697 | A | | 9/1992 | Cajigas ........................... 426/43 |
| 5,358,729 | A | | 10/1994 | Ohkuma et al. ............... 426/567 |
| 5,531,988 | A | | 7/1996 | Paul .............................. 424/93.4 |
| 5,716,615 | A | * | 2/1998 | Cavaliere Vesely et al. . 424/93.4 |
| 5,733,568 | A | | 3/1998 | Ford ............................... 424/433 |
| 5,840,318 | A | | 11/1998 | Marshall et al. ............ 424/282.1 |
| 6,008,027 | A | * | 12/1999 | Langner ......................... 435/174 |
| 6,080,401 | A | | 6/2000 | Reddy et al. .................. 424/93.3 |
| 2002/0192202 | A1 | | 12/2002 | Naidu ......................... 424/93.45 |
| 2003/0147995 | A1 | | 8/2003 | Koss et al. ...................... 426/72 |

FOREIGN PATENT DOCUMENTS

| | | |
|---|---|---|
| WO | WO 99/49877 | 10/1999 |
| WO | WO 00/71138 A2 | 11/2000 |
| WO | WO 00/71139 A2 | 11/2000 |

OTHER PUBLICATIONS

Shimizu et al., "Chemisorbent for medical use. Dialdehydestarc=h-urease conjugate for removal of area as ammonia", *Chemical Abstracts* 1955 103:129004d.
Asher et al., "Projections and measurements of in vivo performance of liquid membrane capsules", *Kidney Int.* 1976 10:S-254-S-258.
Bezkorovainy A., "Probiotics:determinants of survival and growth in the gut [1-3]", *Am. J. Clin. Nutr.* 2001 73(Suppl): 399S-405S.
Bliss et al., "Supplementation with gum arabic fiber increases fecal nitrogen excretion and lowers serum urea nitrogen concentration in chronic renal failure patients consuming a low-protein diet [1-4]", *Am. J. Clin. Nutr.* 1996 63:392-398.
Chang, T.M.S. (Artificial Cells, Chapter 5, in Biomedical Applications of Microencapsulation, edited by Lim, F. CRC Press Florida, pp. 86-100.
Chang T.M.S., "Assessments of clinical trials of charcoal hemoperfusion in uremic patients", *Clin. Neph.* 1979 11:111-119.
Clark et al., Perfusion of Isolated Intestinal Loops in the Management of Chronic Renal Failure, *Trans. Am. Soc. Artif. Intrn. Organs* 1962 8:246-251.
Cummings J.H. et al., Prebiotic digestion and fermentation [1-3], *Am. J. Clin. Nutr.* 2001 73(Suppl) : 415S-420S.
Dunn et al., "Gas Chromatographic Determination of Free Mono-, Di-, and Trimethylamines in Biological Fluids", *Analytical Chemistry* 1976 48:41-44.
Einbacher and Carter, "The Role of the Microbial Flora in uremia", *J. Exp. Med.* 1966 123:239-250.
Okada, K. and Takahashi, S., "Correction by oral adsorbent of abnormal digestive tract milieu in rats with chronic renal failure", *Nephrol. Dial. Transplant.* 1995 10:671-676.
Owadu, A. and Shiigai, T., "Effects of Oral Adsorbent AST-120 Concurrent with a Low-Protein Diet on the Progression of Chronic Renal Failure", *Am. J. Nephrol.* 1996 16:124-127.
Prakash, S. and Chang, T.M.S., "Microencapsulated genetically engineered live *E. coli* DH5 cells administered orally to maintain normal plasma urea level in uremic rats", *Nature Med.* 1996 2:883-887.
Prakash S. and Chang T.M.S., "Preparation and in Vitro Analysis of Microencapsulated Genetically Engineered *E. coli* DH5 Cells for Urea and Ammonia Removal", *Biotechnology and Bioengineering* 1995 46:621-26.
Setala, K., "Bacterial enzymes in uremia management", *Kidney Intl.* 1978 8:S-194-S-202.
Shimizu et al., "Removal of uremic waste metabolites (chiefly urea) by chemically surface-treated dialdehyde starch", *Chemical Abstracts* 1982 97:222900 3p.
Sparks R.E., "Gastrosorbents in the therapy of uremia: Inferences from intestinal loop dialysis", *Kidney Int.* 1975 Suppl 7:S-373-S-376.
Twiss E.E. and Kolff W.J., "Treatment of Uremia by Perfusion of an Isolated Intestinal Loop", *JAMA* 1951 146:1019-1022.

(Continued)

*Primary Examiner* — Ruth Davis
(74) *Attorney, Agent, or Firm* — Licata & Tyrrell P.C.

(57) ABSTRACT

Compositions and methods for improving renal function with *Streptococcus* probiotic bacteria selected for converting nitrogenous waste into non-toxic compounds in vivo are provided. By reducing the levels of nitrogenous wastes, the instant compositions reduce kidney burden.

2 Claims, 3 Drawing Sheets

OTHER PUBLICATIONS

Yatzidis et al., "Newer oral sorbents in uremia", *Clinical Nephrology* 1979 11:105-106.

Waynforth, H.B. and Flecknell, P.A. Nephrectomy. In: Experimental and surgical techniques in the rat. 2nd ed., 1992, Academic Press (Harcourt, Brace, Jovanovich), London, pp. 29, 274-275.

Wrong O., "Various views on anonymity", *Nature Medicine* 1997 2-3.

Holzapfel et al., "Overview of gut flora and probiotics", International Journal of Food Microbiology 1998 41:85-101.

Marteau et al., "Protection from gastrointestinal diseases with the use of probiotics[1-3]", Am J. Clin Nutr 2001 73:430S-436S.

Orrhage and Nord, "Bifidobacteria and Lactobacilli in Human Health", Drugs Exptl. Clin. Res. 2000 XXVI(3):95-111.

Pateras et al., "The Role of Intestinal Perfusion in the Management of Chronic Uremia", Trans. Amer. Soc. Artif. Int. Organs 1964 X:292-295.

von Wright and Salminen, "Probiotics:established effects and open questions", Eur J Gastroenterol Hepatol 1999 11(11):1195-1198.

Bliss et al., "Supplementation with gum arabic fiber increases fecal nitrogen excretion and lowers serum urea nitrogen concentration in chronic renal failure patients consuming a low-protein diet [1-4]", *Am. J. Clin. Nutr*. 1996 63:392-398.

Chang, T.M.S., "Artificial Cells", Chapter 5, in *Biomedical Applications of Microencapsulation*, edited by Lim, F. CRC Press Florida, pp. 86-100.

Clark et al., "Perfusion of Isolated Intestinal Loops in the Management of Chronic Renal Failure", *Trans. Am. Soc. Artif. Intrn. Organs* 1962 8:246-251.

Dunn et al., "Gas Chromatographic Determination of Free Mono-, Di-, and Trimethylamines in Biological Fluids", *Analytical Chemistry* 1976 48:41-44.

Einbacher and Carter, "The Role of the Microbial Flora in uremia", *J. Exp. Med*. 1966 123:239-250.

Friedman et al., "Hypertrigylceridemia Responsive to Charcoal Sorption", *Proc. Clin. Dia. Trans. Forum* 1977 7:183-184.

Goldenhersh et al., "Effect of microencapsulation on competitive adsorption in intestinal fluids", *Kidney Int*. 1976 10:S251-S253.

Gotch et al., "Theoretical Considerations on Molecular Transport in Dialysis and Sorbent Therapy for Uremia", *Journal of Dialysis* 1976-1977 1(2):105-144.

Kjellstrand et al., "On the Clinical use of Microencapsulated Zirconium Phosphate-Urease for the Treatment of Chronic Uremia", *Trans. Am. Soc. Artif. Intern. Organs* 1981 27:24-29.

Kolff, W.J., "Longitudinal perspectives on sorbents in uremia", *Kidney Int*. 1976 10:S211-S214.

Nagano et al., "Pharmacological properties of chitosan-coated dialdehyde cellulose (chitosan DAC), a newly developed oral adsorbent (II). Effect of chitosan DAC on rats with chronic renal failure induced by adriamycin", Medline Abstract UI 96058336 1995.

Niwa et al., "Indoxyl Sulfate and Progression of Renal Failure: Effects of a Low-Protein Diet and Oral Sorbent on Indoxyl Sulfate Production in Uremic Rats and undialyzed Uremic Patients", *Miner. Electr. Metab*. 1997 23:179-184.

Okada, K. and Takahashi, S., "Correction by oral adsorbent of abnormal digestive tract milieu in rats with chronic renal failure", *Nephrol. Dial. Transplant*. 1995 10(5):671-676.

Owadu, A. and Shiigai, T., "Effects of Oral Adsorbent AST-120 Concurrent with a Low-Protein Diet on the Progression of Chronic Renal Failure", *Am. J. Nephrol*. 1996 16(2):124-127.

Prakash, S. and Chang, T.M.S., "Microencapsulated genetically engineered live *E. coli* DH5 cells administered orally to maintain normal plasma urea level in uremic rats", *Nature Med*. 1996 2:883-887.

Prakash, S. and Chang, T.M.S., "Preparation and in Vitro Anaylsis of Microencapsulated Genetically Engineered *E. coli* DH5 Cells for Urea and Ammonia Removal", *Biotechnology and Bioengineering* 1995 46:621-626.

Setala, K., "Bacterial enzymes in uremia management", *Kidney Intl Suppl*. 1978 8:S194-202.

Shimizu et al., "Removal of uremic waster metabolites (chiefly urea) by chemically surface-treated dialdehyde starch", *Chemical Abstracts* 1982 97:222903.

Gibson, G.R. and Roberfroid, M.B. "Dietary Modulation of the Human Colonic Microbiota: Introducing the Concept of Prebiotics" Journal of Nutrition 1995 vol. 125: 1401-1412.

Office Communication Dated Sep. 3, 2009 from U.S. Appl. No. 10/936,262, filed Sep. 8, 2004.

Office Communication Dated Aug. 21, 2008 from U.S. Appl. No. 10/936,262, filed Sep. 8, 2004.

Office Communication Dated Mar. 13, 2008 from U.S. Appl. No. 10/936,262, filed Sep. 8, 2004.

Office Communication Dated Aug. 29, 2007 from U.S. Appl. No. 10/936,262, filed Sep. 8, 2004.

Office Communication Dated Mar. 16, 2007 from U.S. Appl. No. 10/936,262, filed Sep. 8, 2004.

Office Communication Dated Jul. 25, 2006 from U.S. Appl. No. 10/936,262, filed Sep. 8, 2004.

Office Communication Dated Feb. 8, 2006 from U.S. Appl. No. 10/936,262, filed Sep. 8, 2004.

Office Communication Dated Oct. 31, 2005 from U.S. Appl. No. 10/936,262, filed Sep. 8, 2004.

Office Communication Dated Sep. 22, 2009 from U.S. Appl. No. 10/936,262, filed Sep. 8, 2004.

Office Communication Dated Nov. 9, 2006 from U.S. Appl. No. 10/936,262, filed Sep. 8, 2004.

\* cited by examiner

COMPOSITIONS AND METHODS IMPROVING RENAL FUNCTION

CROSS REFERENCE TO RELATED APPLICATIONS

This application is a continuation-in-part of U.S. patent application Ser. No. 10/803,211, filed Mar. 18, 2004 now abandoned, which is a continuation-in-part of U.S. patent application Ser. No. 10/689,359, filed Oct. 20, 2003, which is a continuation-in-part of U.S. patent application Ser. No. 09/855,346, filed May 15, 2001, now U.S. Pat. No. 6,706,287, which is a continuation-in-part of U.S. patent application Ser. No. 09/577,011, filed Apr. 20, 2000, now U.S. Pat. No. 6,706,263, which claims the benefit of priority from U.S. Provisional Application 60/131,774 filed Apr. 30, 1999. This application is also a continuation-in-part of U.S. patent application Ser. No. 10/676,622, filed Sep. 30, 2003 now U.S. Pat. No. 7,026,160 and U.S. patent application Ser. No. 10/676,558, filed Sep. 30, 2003, which are continuations-in-part of U.S. patent application Ser. No. 09/855,346, filed May 15, 2002, now U.S. Pat. No. 6,706,287, which is a continuation-in-part of U.S. patent application Ser. No. 09/557,011, filed Apr. 20, 2000, now U.S. Pat. No. 6,706,263, which claims the benefit of priority from U.S. Provisional Application 60/131,774 filed Apr. 30, 1999.

INTRODUCTION

This work is partly funded from the Small Business Innovation Research (SBIR) grant award from the National Institutes of Diabetes, Digestive and Kidney (NIDDK) Diseases, National Institute of Health (NIH), Bethesda, Md. Grant No: 1R44DK61873-01.

BACKGROUND OF THE INVENTION

Kidney disease is ranked fourth among the major diseases in the United States afflicting over 20 million Americans. More than 90,000 patients die each year because of kidney diseases. In recent years the number of chronic kidney failure patients has increased about 11 percent annually. About 80,000 Americans on dialysis die of various complications each year and more than 27,000 are on waiting lists for kidney transplants each year with only about 11,000 of these patients receiving transplants. Further, nearly 350,000 Americans suffer from end stage renal disease (ESRD), which is the final stage in chronic renal failure.

In normal, healthy humans, metabolic waste nitrogen is primarily excreted via the kidneys as urea, uric acid creatinine, etc. in the urine. However, in individuals with kidney disease, as well as a number of other diseases such as inborn errors in urea cycle enzyme deficit, waste nitrogen accumulates in the body thereby manifesting toxic symptoms. Hyperammonium can lead to mental retardation and, in severe cases, coma.

Uremic toxins accumulate during development of renal failure. Uremic toxins are generated from a number of sources including diet, chemotherapy, diabetes and metabolic disorders. Any number of low-carbohydrate and high-protein diets is being touted today as the answer for weight problems and obesity. More and more people are cutting carbohydrates from their diets and eating more meat, fish, poultry and dairy products to reduce body fat. However, too much protein can lead to kidney problems and urinary tract problems, affecting a person's ability to stay properly hydrated during times of increased activity which also increases the risk of heat stress. Additionally, high-protein diets actually accelerate calcium loss form bones and increase the risk of osteoporosis, leading to an increase in stress fractures, ankle fractures and vertebral fractures. High protein diets also lead to the condition called ketosis, or the accumulation of ketone bodies.

Currently hemo- or peritoneal-dialysis and renal transplant are the only treatment modalities. However, the economic costs of these treatment modalities are extremely high. For example, in 1996 in the United States alone, the annual cast of ESRD treatment was over 14 billion dollars. In developing and underdeveloped countries with low health care budgets, ESRD patients are deprived access to such treatments due to their high costs. Accordingly, there is a need for alternative modalities of treatment for uremia.

A number of treatment attempts have been based on the use of the bowel as a substitute for kidney function. During a normal digestive process the gastrointestinal tract delivers nutrients and water to the bloodstream and eliminates some waste products and undigested materials through the bowel. The intestinal wall regulates absorption of nutrients, electrolytes, water and certain digestive aiding substances such as bile acids. The intestinal wall also acts as a semi-permeable membrane allowing small molecules to pass from the intestinal tract into the bloodstream and preventing larger molecules from entering the circulation.

Nitrogenous wastes such as urea, uric acid, creatinine and uric acid, along with several other small and medium molecular weight compounds, flow into the small intestine and equilibrate across the small intestine epithelium. Studies of intestinal dialysis have shown a daily flow of 71 grams of urea, 2.9 grams of creatinine, 2.5 grams of uric acid and 2.0 grams of phosphate into the intestinal fluid (Sparks (1975) *Kidney Int. Suppl.* (Suppl 3) 7:373-376). Accordingly, various invasive and noninvasive attempts including external gut fistula, intestinal dialysis, induced diarrhea, and administration of oral sorbents and/or encapsulated urease enzyme have been made to extract uremic waste from the gastrointestinal tract (Twiss and Kolff (1951) *JAMA* 146:1019-1022; Clark, et al. (1962) *Trans. Am. Soc. Artif. Intrn. Organs* 8:246-251; Pateras, et al. (1965) *Trans. Am. Soc. Artif. Intrn. Organs* 11:292-295; Shimizu, et al. (1955) *Chemical Abstracts* 103:129004; Kjellstrand, et al. (1981) *Trans. Am. Soc. Artif. Intern. Organs* 27:24-29; Kolff (1976) *Kidney Int.* 10:S211-S214).

In addition, genetically engineered *E. herbicola* cells have been encapsulated and demonstrated to convert ammonia into usable amino acids for the cells before being eliminated via the bowel. Microencapsulated genetically engineered *E. coli* DH5 cells have also been shown to be effective in removal of urea and ammonia in an in vitro system and in a uremic rat animal model (Prakash and Chang (1955) *Biotechnology and Bioengineering* 46:621-26; Prakash and Chang (1996) *Nature Med.* 2:883-887). However, administration of genetically engineered bacteria poses regulatory and safety concerns and raises ethical issues which may lead to noncompliance by patients.

The human gastrointestinal tract harbors a complex microbial ecosystem containing a large number and variety of bacteria. The resident bacterial population in the human gastrointestinal tract has a major impact on gastrointestinal function and thereby on human health and well-being. Among these, some bacteria are opportunistic and considered to be detrimental and cause adverse conditions such as diarrhea, infections, gastroenteritis and endotoxaemia, while some bacteria species are considered as "probiotic", in that they perform beneficial functions for the human organism (Holzapfel, et al. (1998) *Int. J. Food Microbiol.* 41(2): 85-101).

Among the probiotic bacteria, *Bifidobacteria* species are the most prominent. *Bifidobacteria* species, when in live and viable form, stimulate the immune system and exert a competitive exclusion of pathogenic and putrefactive bacteria, reduce the amounts of ammonia and cholesterol in the blood, and promote absorption of minerals. In addition, *Bifidobacteria* have been suggested to exert a preventive action against colon cancer, by reducing the activity of some enzymes that convert procarcinogen substances into carcinogen substances (von Wright, et al. (1999) *Eur. J. Gastroenterol. Hepatol.* 11(11):1195-1198).

The lactic bacteria include *Lactobacillus bulgaricus, Lactobacillus acidophilus, Lactobacillus casei, Lactobacillus plantarum* and *Streptococcus faecium. Streptococcus thermophilus* are also considered probiotic. These bacteria produce antagonist effects against pathogenic microorganisms, stimulate the immune system, improve lactose digestion, perform a lypolytic activity making fats more digestible, reduce plasmatic values of cholesterol, protect the intestinal mucosa ensuring an even assimilation of the nutritive substances, produce polysaccharides that are active on some tumors, and reduce viability of some enzyme-producing microorganisms catalysing conversion of procarcinogen substances into carcinogenic substances.

It is believed that the probiotic bacteria exert their effects in a synergistic manner to curtail and retard the growth of pathogenic/detrimental bacteria of the gut (Marteau, et al. (2001) *Am. J. Clin. Nutr.* 73(2 Suppl):430S-436S; Cummings, et al. (2001) *Am. J. Clin. Nutr.* 73(2 Suppl):415S-420S).

The intestinal bacteria flora can be reduced become unbalanced or be eliminated in patients undergoing antibiotic treatment and other therapies, and in individuals suffering from inflammatory intestinal diseases, kidney disease and liver disease. In addition, it has been shown that during normal aging the *Bifidobacteria* population is reduced while the concentration of pathogenic and putrefactive bacteria concamitantly increases (Orrhage, et al. (2000) *Drugs Exp. Clin. Res.* 26(3):95-111).

It is also known that beneficial effects of microbes such as the *Bifidobacterium* species are in part due to their ability to ferment nondigestible sugars, known as prebiotics, present in the colon. A prebiotic is a non-digestible food ingredient that beneficially affects the host by selectively stimulating the growth and/or the activity of one or a limited number of bacteria in the colon. Prebiotics are typically thought of as carbohydrates of relatively short chain length. Prebiotics are like other carbohydrates that reach the cecum, such as non-starch polysaccharides, sugar alcohols, and resistant starch, in being substrates for fermentation. They are, however, distinctive in their selective effect on the microflora and are effective only when they reach the cecum (Bezkorovainy (2001) *Am. J. Clin. Nutr.* 73(2 Suppl):399S-405S).

U.S. Pat. No. 5,733,568 teaches the use of microencapsulated *Lactobacillus* bacteria for treatment of antibiotic associated or other acute and chronic diarrhea as well as for skin and vaginal yeast infections. The microencapsulation is said to prevent inactivation of the bacillus and to deliver it to the intestine as well as to avoid lactose intolerance seen in said diarrheas.

U.S. Pat. No. 5,032,399 teaches the use of species of *Lactobacillus acidophilus* to adhere to intestinal mucosa and thereby reduce gastrointestinal side effects of antibiotic therapy that reduces beneficial bacteria population.

U.S. Pat. No. 5,145,697 discloses powdered yogurt formulations containing *S. thermophilus*. Similarly, U.S. Pat. No. 4,427,701 teaches a frozen yogurt product containing *S. thermophilus*. However, these references do not teach any special features of the *S. thermophilus* strain employed.

U.S. Pat. No. 5,531,988 teaches, in addition to beneficial bacteria, use of immunoglobulin in the composition as a dietary supplement.

U.S. Pat. No. 5,840,318 also teaches a beneficial bacterial composition that can modulate the immune system of animals.

U.S. Pat. No. 6,080,401 teaches that the speed of treatment using herbal medicines can be improved by combining the herbal medicine with probiotic microorganisms. However, this reference does not teach any special features of the probiotics employed.

Use of probiotics such as *Lactobacillus acidophilus* has been suggested to curtail the bacterial overgrowth and the accumulation of uremic toxins and carcinogenic compounds. Unabsorbable carbohydrate in the diet of uremic patients has also been shown to increase fecal nitrogen. Use of lactulose and dietary fiber has also been shown to reduce plasma urea 11 to 27% and increase fecal nitrogen excretion to 39 to 62% (Wrong (1997) *Nature Medicine* 2-3).

SUMMARY OF THE INVENTION

The present invention is a composition for improving renal function. The composition contains at least one probiotic bacterium, wherein the probiotic bacterium is a *Streptococcus* selected for converting nitrogenous wastes into non-toxic compounds. In particular embodiments, the composition of the invention is used in a method for improving renal function a subject. The method of the embodiment involves administering to a subject in need of treatment the composition of the invention thereby improving renal function in the subject.

DETAILED DESCRIPTION OF THE INVENTION

Figure 1A:
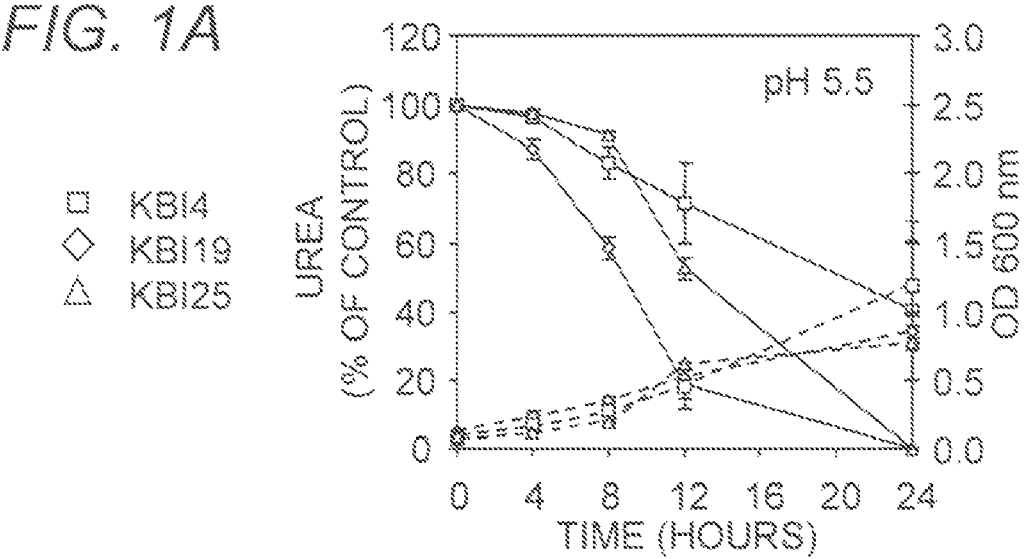
FIG. 1 shows the urea hydrolysis by *S. thermophilus* strains at pH 5.5 (FIG. 1A), pH 6.3 (FIG. 1B), and pH 7.5 (FIG. 1C), AIF, 100 mg/dL urea with 100 μM $NiCl_2$. Data is presented as mean±SEM, n=3-9.

In kidney failure there is a decrease in the glomerular filtration rate and the kidneys are unable to maintain homeostasis of the blood. Homeostatic balance of water, sodium, potassium, calcium and other salts is no longer possible and nitrogenous wastes are not excreted. Retention of water causes edema and as the concentration of hydrogen ions increases, acidosis develops. Nitrogenous wastes accumulate and a condition referred to as uremia develops in the blood and tissue. Uremic toxins can be defined as solutes that: (I) are normally excreted by healthy kidneys, (ii) accumulate progressively during the development of renal failure so that their concentration increases, and (iii) inhibit various physiologic and biochemical functions; as a whole, they contribute to a complex set of clinical symptoms that comprise the Uremic Syndrome. Examples of uremic toxins include, but are not limited to, ammonia, urea, creatinine, phenols, indoles, and middle molecular weight molecules. More specifically, in uremia, the concentration of nitrogenous wastes such as serum creatinine, blood urea nitrogen (BUN), uric acid, and guanidine compounds such as N-methyl guanidine (NMG) and guanidino succinic acid, (GSA) are significantly altered with accompanying abnormalities in acid-base equilibrium, electrolytes and water retention. In addition there are several known and unknown substances of low and middle molecular weight which have been identified as uremic toxins which also accumulate. If untreated this acidosis and uremia can cause coma and eventually death.

The introduction of renal dialysis has contributed to rapid progress in the clinical treatment of renal failure and elucidation of uremia. When a subject has mild kidney failure where the serum creatinine level is less than 400 µmol/L, the subject does not require renal replacement therapy such as dialysis or renal transplant. However, in general, when the serum creatinine level rises to 900 µmol/L, the subject needs routine dialysis or a kidney transplant to survive.

Dialysis can serve as a lifetime therapy for ESRD patients. Phosphate binders such as calcium acetate, calcium carbonate or aluminum hydroxide are generally prescribed for uremic patients receiving dialysis to reduce elevated phosphate levels. In general, however, dialysis is very expensive, inconvenient, time consuming and may occasionally produce one or more side effects. With a successful kidney transplant, a subject can live a more normal life with less long-term expense. However, there are also high costs associated with transplant surgery, the recovery period and the continuous need for anti-rejection medications. Further, there are often times a shortage of suitable donors. Accordingly there is a need for alternative strategies for improving renal function.

Nitrogenous wastes which accumulate in uremia flow into the gut by diffusion. Accordingly, the present invention provides a formulation of commensal and food grade bacteria known as probiotic bacteria, that when ingested become intestinal or gut flora and catabolize nitrogenous wastes into non-toxic compounds. Instillation of such probiotic bacteria permit reduction in frequency and even elimination of the need for dialysis. Probiotic bacteria of the present invention are living microorganisms that are naturally present in the gastrointestinal tract of humans and animals. They are beneficial bacteria that enhance the body's defenses against a number of health conditions.

More specifically, the present invention is a composition containing at least one probiotic bacterium, wherein the probiotic bacterium is a *Streptococcus* species selected for converting nitrogenous wastes accumulated in the subject due to renal insufficiency into nontoxic compounds. As used herein, the term subject is meant to include humans, companion animals (e.g., cats and dogs), livestock (e.g., pigs, cows, horses, and sheep) and zoological animals. In renal patients, nitrogenous solutes traverse intestinal capillaries into the bowel through diffusion. The composition of the present invention can be administered orally, or through any other appropriate manner so that the selected bacteria are instilled into the gastrointestinal tract of the subject and nitrogenous wastes are reduced.

Figure 1B:
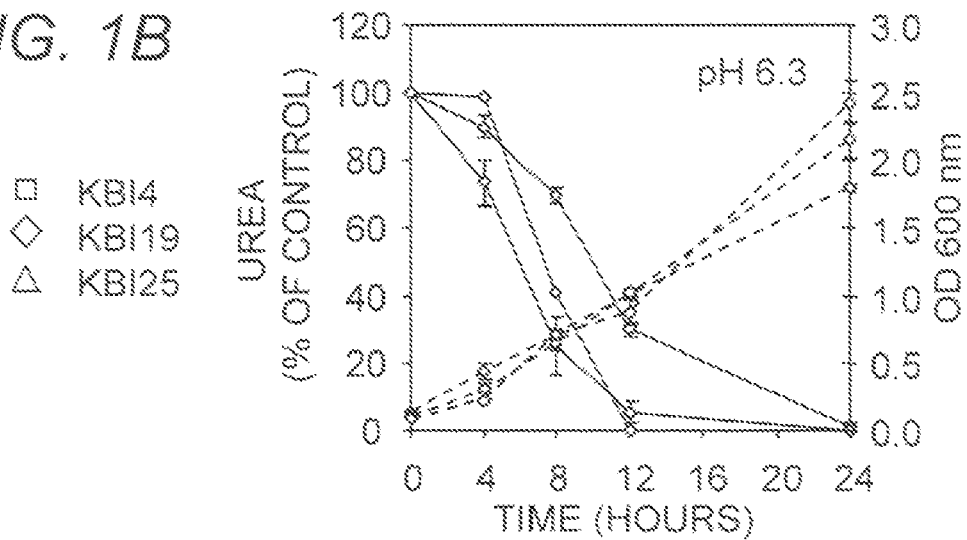
Figure 1C:
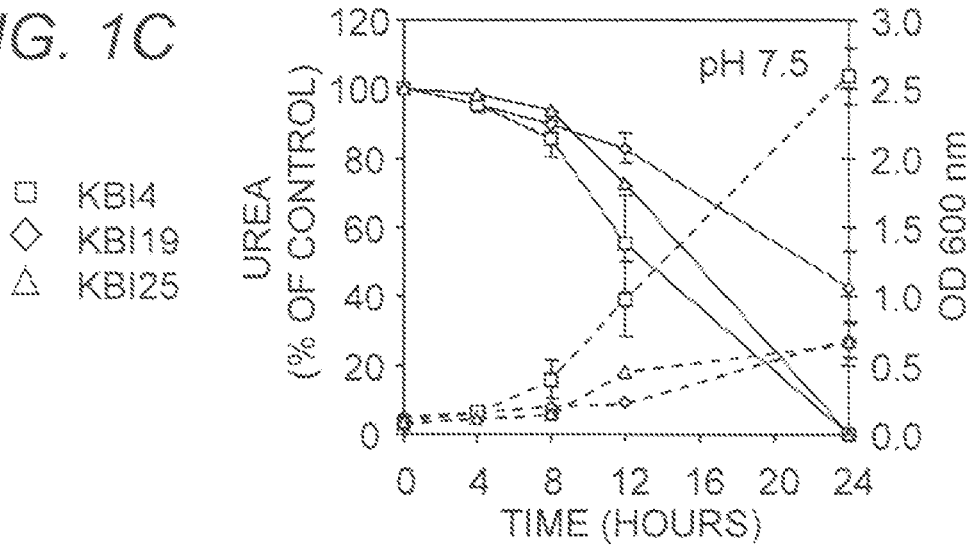

The selected bacteria are live bacteria which consume excess urea, creatine, and "uremic" solutes. In particular embodiments, the selected bacteria are of the genus *Strepto-* *coccus*. Suitable streptococcal species for use in the compositions of the invention include, but are not limited to *S. faecium, S. thermophilus*, and *S. lactis*, with particular embodiments embracing *S. thermophilus*. Three exemplary *S. thermophilus* strains, namely strains KB4, KB19 and KB25, isolated from different sources (e.g., commercial yogurt and Dahl yogurt from India) were characterized in vitro by assessing their ability to catabolize urea while proliferating in the simulated gastric juice (Table 1) and in simulated intestinal fluid (FIGS. 1A-1C).

TABLE 1

| Strain | pH | Survival (churn) | | | |
| --- | --- | --- | --- | --- | --- |
| | | 0 Hours | 1 Hour | 2 Hours | 3 Hours |
| KB19 | 1.4 | $10^{10}$ | 0 | 0 | 0 |
| | 2.0 | $10^{10}$ | 0 | 0 | 0 |
| | 2.4 | $10^{10}$ | $10^8$ | $10^8$ | $10^4$ |
| | 3.0 | $10^{10}$ | $10^8$ | $10^8$ | $10^6$ |
| KB4 | 1.4 | $10^{10}$ | $10^3$ | 0 | 0 |
| | 2.0 | $10^{10}$ | $10^3$ | 0 | 0 |
| | 2.4 | $10^{10}$ | $10^5$ | $10^4$ | $10^4$ |
| | 3.0 | $10^{10}$ | $10^{10}$ | $10^{10}$ | $10^8$ |
| KB25 | 1.4 | $10^{10}$ | 0 | 0 | 0 |
| | 2.0 | $10^{10}$ | 0 | 0 | 0 |
| | 2.4 | $10^{10}$ | ND | ND | $10^6$ |
| | 3.0 | $10^{10}$ | ND | ND | $10^7$ |

Figure 2A:
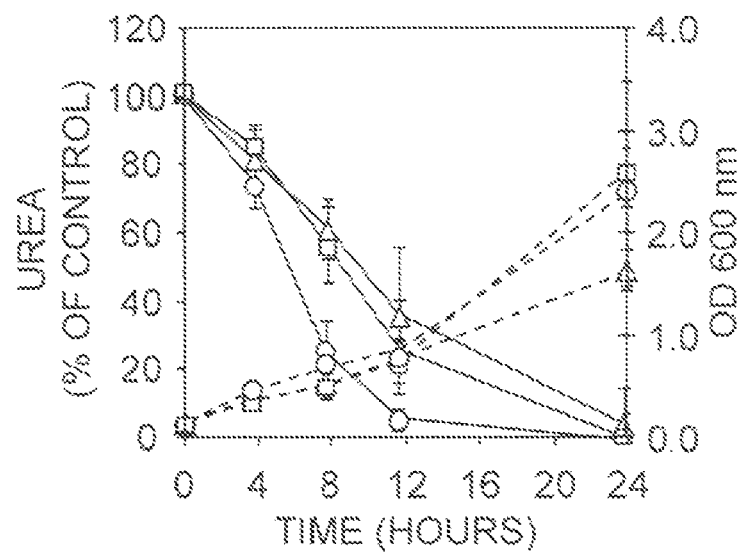
FIG. 2 shows urea hydrolysis by *S. thermophilus* strains KB19 (FIG. 2A), KB4 (FIG. 2B), and KB25 (FIG. 2C) at concentrations of urea characteristic of uremic blood levels. AIF, pH 6.3, with 100 μM $NiCl_2$. Data is presented as mean±SEM, n=3-5.
Figure 2B:
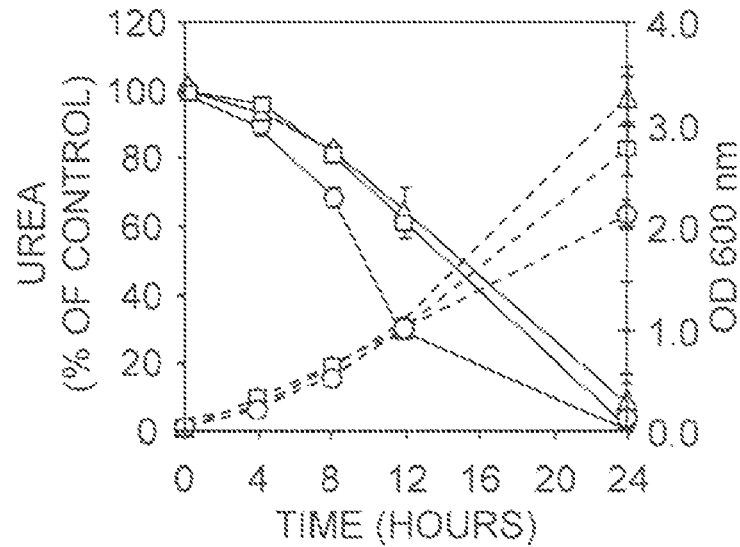
Figure 2C:
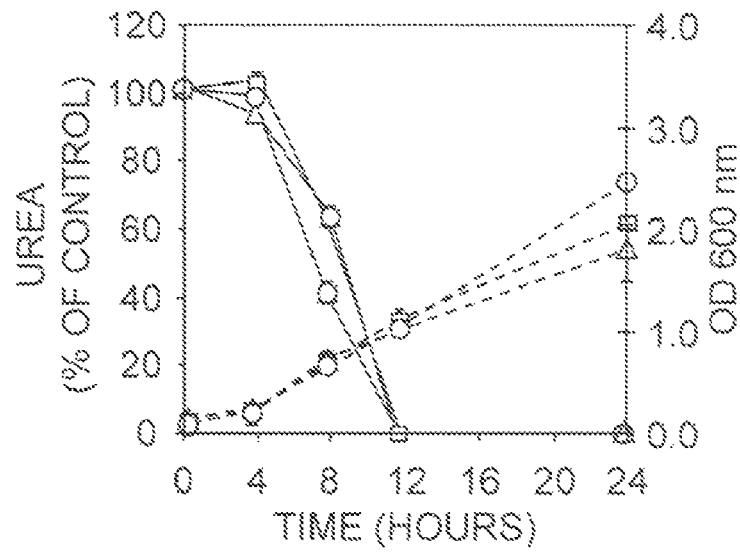
Figure 3:
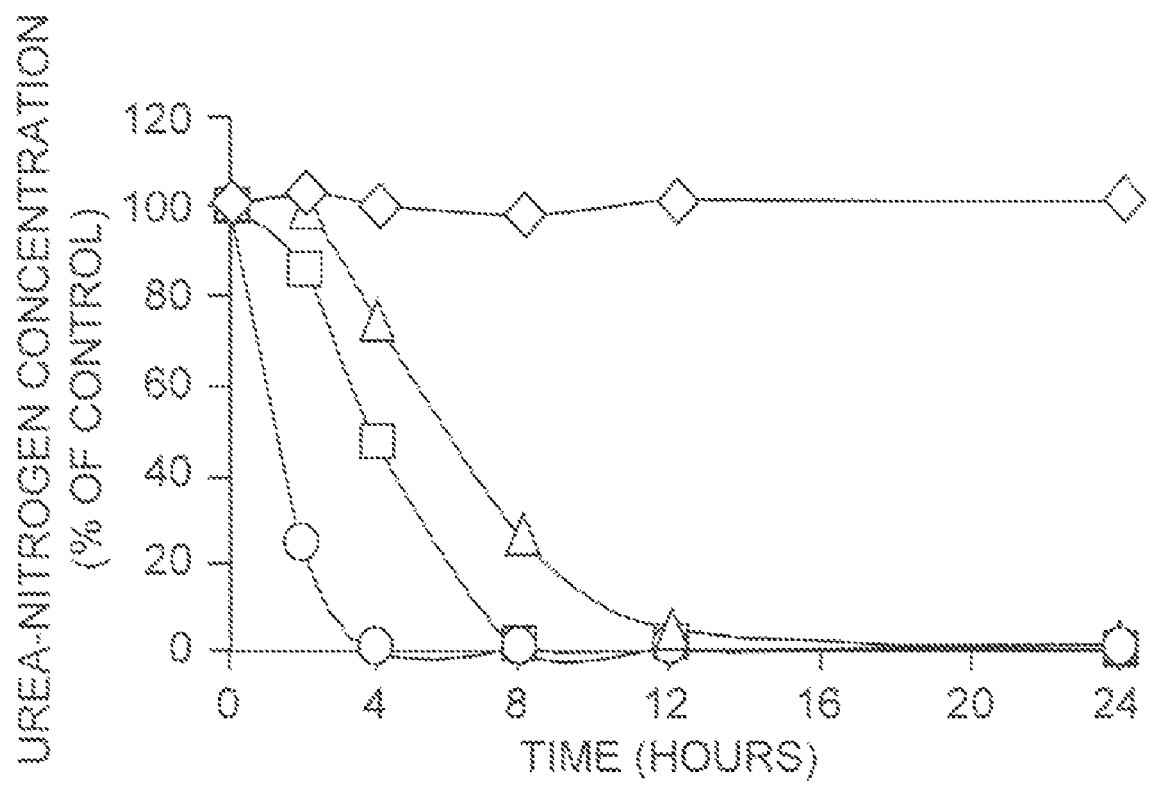
FIG. 3 shows ureolysis and urea-nitrogen concentration degradation rates for different bacterial strains. Diamonds, control; circles, *Bacillus pasteurii* ATCC 6453 triangle, *Streptococcus thermophilus* KB19; squares, *E. coli* strain DH5α transformed with a multi-copy plasmid bearing the *Klebsiella aerogenes* urease operon.

All three strains proliferated in the fed state simulated artificial intestinal fluid (AIF) in the pH range from 5.5 to 7.5, characteristic of the colon environment; used urea as a sole nitrogen source; and catabolized urea in the present of other nitrogen sources. Urea hydrolysis was growth- and pH-dependent. FIGS. 2A-2C show that KB19, KB4, and KB25, respectively, are efficient in hydrolyzing urea in blood. Under all the conditions tested, the rate of urea hydrolysis was strain dependent permitting selection of the best candidate for uremic applications. One selected isolate, *S. thermophilus* KB19, reduced urea concentrations from 300 mg/dL, to 20 mg/dL within 24 hours at pH 6.3 when inoculated at initial density of $10^9$ cfu/mL KB19 survived 3 hours in acidic pH 3.0 with only tow logs loss in cfu and was able to pass through bile. Further, it was found that ureolysis by KB19 was comparable to other urea utilizing bacteria such as *B. pasteurii* and genetically engineered urealytic *E. coli* (FIG. 3) when assessed in AIF. AIF was prepared according to U.S. pharmacopoeia with modifications (addition of 1% dextrose, 100 µM $NiCl_2$, 10% MRS broth and 100 mg/dL urea and, for growth of the plasmid bearing *E. coli*, 0.01% ampicillin). Bacterial strains were inoculated into modified AIF at the initial density of $10^9$ cfu/mL for *S. thermophilus* and *B. pasteurii* and $10^8$ cfu/mL for *E. coli* and incubated at 37° C. Aliquots were taken at 0, 2, 4, 8, 12 and 24 hours and urea nitrogen and optical density (OD) data were recorded. Within 24 hours all strains removed 100% of urea from the system. Therefore, *S. thermophilus* KB19 is advantageously used in a composition of the present invention to remove nitrogenous wastes such as urea. In addition, strain KB19 did not exhibit any resistance to commonly used antibiotics.

In particular embodiment, the *Streptococcus* probiotic bacterium is selected, adapted or trained to convert nitrogenous wastes into non-toxic compounds. Generally, selection or adaptation is achieved by exposing the *Streptococcus* to increasing amounts of the nitrogenous waste of interest (e.g., urea, creatinine, uric acid and ammonia) to select for bacteria capable of metabolizing high concentrations of the nitrogenous waste into non-toxic compounds. For example, it has been found that *Streptococcus thermophilus* can be trained to express elevated levels of urease by sequential passage of the strain on increasing amounts of urea, e.g., a single colony growing on 0.5% urea is selected and applied to medium containing 1.0% urea, a single colony growing on 1.0% urea is selected and applied to medium containing 2.0% urea, etc. Using such a method, a *S. thermophilus* strain having the ability to grow on 5% urea was isolated. This strain proliferated in artificial intestinal fluid (AIF, US Pharmacopeia) in the pH range of 5.5 to 7.5, characteristic of the colon environment; used urea as a sole nitrogen source; and catabolized urea in the presence of other nitrogen sources. It was found that urea hydrolysis was growth- and pH-dependent and that urea concentrations could be reduced by this strain from 300 mg/dL to 20 mg/dL within 24 hours at pH 6.3 when inoculated in AIF at an initial density of $10^9$ cfu/mL. Moreover, this strain survived 3 hours in acidic pH 3.0 with only a one-log loss in cfu and was able to pass through bile. In addition, this strain did not appear to exhibit any resistance to eight commonly used antibiotics.

In addition to a *Streptococcus* selected for converting nitrogenous wastes into non-toxic compounds, the present composition can further contain other probiotic bacteria including, but not limited to, *Lactobacillus* sp. such as *L. acidophilus, L. bulgaricus, L. casei, L. plantarum*, or *L. ruteri* or *L. sporogenes; Bacillus* sp. such as *B. pasteurii*; and *Bifidobacterium* sp. such as *B. adolescentis, B. infantis, B. longum, B. thermophilus*, or *B. bifidum*. In a particular embodiment, the composition further contains one or more of *L. bulgaricus, L, acidophilus, B. longum* or *B. bifidum*.

It has been found that the probiotic bacteria are more effective in ranges of from $10^9$ to $10^{11}$ cfu. For instance, *S. thermophilus* is of particular use between $10^{10}$ to $10^{11}$ cfu, whereas *Lactobacillus acidophilus* is useful between $10^9$ to $10^{10}$ cfu and *B. longum* is useful between $10^9$ to $10^{10}$ cfu. One skilled in the art can routinely determine the appropriate ranges of the probiotic bacteria based upon desired application and use.

In addition to probiotic bacteria, certain embodiments provide that the instant composition contains at least one vitamin component and/or at least one mineral component. In this aspect the composition may take the form of an enhanced multi-vitamin or calcium supplement. Moreover, the composition of the present invention can further contain sorbents with specific adsorption affinities for uremic toxins such as creatinine, uric acid, phenols, indoles, middle molecular weight molecules and inorganic phosphate along with a water sorbent, for use in the alleviation of uremia. Adsorbents of particular use include locust bean gum with a specific adsorption affinity for creatinine and urea, activated charcoal with a specific adsorption affinity for creatinine, guanidines, phenol, indican and middle molecular weight undefined components, or water absorbents such as psyllium fiber, guar gum and locust bean gum. Compositions of the present invention can further contain a phosphate binding agent such as aluminum hydroxide gel, calcium carbonate or calcium acetate, or magnesium hydroxide gel. In another embodiment, the composition contains one or more prebiotics such as inulin, a fructan oligosaccharide, lactulose and other vegetable fibers.

A composition of the present invention can be enteric coated and/or microencapsulated. Enteric coating of some or a part of the composition allows the probiotic bacterial source to be delivered at the ideal and colonic regions of the bowel where maximal resorption of uremic solutes and other molecules are found to occur. This is preferably achieved via an enteric coating material that disintegrates and dissolves at a pH of 7.5 or higher. Examples of enteric coatings with these characteristics include, but are not limited to, Zein, polyglycolactic acid, polylactic acid, polylactide-co-glycolide and similar coating materials. Enteric coatings also enable delivery of sorbents to their site of action in relatively native form without binding of various digestive materials to the sorbents prior to reaching the target region. In addition to delivery via capsule or pill form, the compositions of the present invention can be in the form of a liquid, paste or other suitable form. For example, the instant composition can be delivered orally via an emulsion or paste mixed with an easy to eat food. The oral delivery of the compositions can also be via ready to eat food or other nutritional product, e.g., nutriceuticals, dietary supplements, and powders, health bars, yogurts, dry foods, and pet formulations.

Given that the probiotic bacteria of the instant compositions (when instilled into the gastrointestinal tract of a subject) can function to restore normal balance between beneficial bacteria and detrimental bacteria, and metabolize nitrogenous waste such as urea and ammonia to remove excess waste products, the instant composition is useful for reducing the burden on the kidney and therefore improving renal function. Thus, the present invention is also a method for improving renal function by administering to a subject in need of treatment, an effective amount of a composition of the present invention. An "effective amount" as used herein is an amount necessary to achieve a selected result. For example, an effective amount of a probiotic bacterium-containing composition useful for improving renal function is an amount that, e.g., decreases the levels of nitrogenous wastes thereby reducing the kidney burden and/or alleviating symptoms of uremia. Reduction of nitrogenous wastes is indicated via blood, urine or fecal sample testing wherein a reduction in BUN levels or serum creatinine levels of the blood, urine or fecal samples as compared to initial or control levels indicates effective treatment. By alleviation of symptoms of uremia, it is meant that the composition removes sufficient levels of uremic toxins such that a subject suffering from uremia either does not require dialysis, requires dialysis less frequently or for shorter durations, or does not require initiation of dialysis as soon as would be needed without treatment. Such an amount is readily determined without undue experimentation by those skilled in art.

Subjects who would benefit from use of the instant composition and method include those suffering from renal insufficiency and inborn error of urea metabolism, as well as subjects with liver insufficiency and gastrointestinal disorders and diseases. The compositions can also be administered to a subject to alleviate the symptoms of uremia caused by chemotherapeutic drug programs, diabetic kidney related failures or kidney disease. The composition of the present invention can be administered via any suitable means including but not limited oral administration of the selected bacteria as s pharmaceutical composition or food stuff, injection, surgical implantation, or intranasal administration. It is preferred that the compositions of the present invention be administered to the subject on a routine basis such as one or more times daily over a period of time.

Toxic nitrogenous waste products can accumulate in the intestinal tract of a subject when the normal balance of intestinal microbes is disrupted. These products will also tend to accumulate in the gastrointestinal tract in any condition which disrupts the kidneys ability to excrete the build up of nitrogenous waste products in the blood, thereby resulting in the diffusion of the nitrogenous waste products from the circulating blood into the bowel. Exemplary conditions that effect nitrogen metabolism include, but are not limited to, high protein consumption, chemotherapy, metabolic diseases, defects in protein metabolism, and nucleic acid metabolism. Diabetes, kidney failure, and liver disease, as well as other conditions can result in the build up of toxic nitrogenous compounds in the blood such as specifically chemotherapy for cancer, HIV, and AIDS. Therefore, the instant compositions can also be administered orally to subjects in need thereof to decrease the build-up of toxins and metabolic wastes and/or to inhibit or decrease the over growth of undesirable bacteria in the subject. The precise amount of the compositions of the present invention ingested by a subject may be decided according to the judgment of a practitioner or dietician and each subject's circumstances.

The present invention is further illustrated by the following non-limiting examples.

EXAMPLE 1

Sprague-Daly rats weighing 281.20±41.6 gm were subjected to 5/6th nephrectomy after measurement of baseline weight, BUN, serum creatinine, urine volume and fecal flora composition. The study group consisted of 36 nephrectomized rats and 6 controls. After a two-week post surgery stabilization, cohorts of six rats were fed standard rat chow plus one of the following regimens: 1) placebo, 2) *B. pasteurii* 3) *L. sporogenes*, 4) *L. acidophilus, L. bulgaricus; Bifidus, S. thermophilus, L. casei*, and *L. reuteri*, 5) *L. acidophilus, L. bulgaricus, Bifidus, S. thermophilus* and 6) *S. boulardii*. Subsequent blood, urine, and fecal measurements were obtained every 30 days for a total of 120 days.

Rats fed *B. pasteurii* and *L. sporogenes* had lower BUN levels (62.0±21 mg/dl and 63.0±26 mg/dl, respectively) compared with placebo (99.0±46 mg/dl) a reduction of (38 and 37%). Serum creatinine levels were similarly reduced in rats fed with *B. pasteurii* and *L. sporogenes* (0.9±0.25 mg/dl and 0.9±0.2 mg/dl, respectively) compared to placebo (1.5±0.56 md/dl) a reduction of 40% in both groups. Feeding increased the fecal count for the appropriate group of bacteria in all groups at eight weeks. These results indicate that *B. pasteurii* and *L. sporogenes* administered orally as a component of a dietary supplement metabolize urea and creatinine in subjects.

In a second study using a rat model of CRF (5/6 nephrectomy) 6 non-pathogenic microorganisms (MO) were tested for use in a probiotic product. Sixty rats had 5/6 nephrectomies performed. Baseline creatinine levels (Scr), BUN were measured and creatinine clearance (CrCl) calculated. Rats (18 male and 18 female) with sufficient renal impairment (Scr=1.0±0.4) were distributed into 6 matched groups (GP), ANOVA showed no significant difference between groups (p=0.516) at baseline. Rats were individually caged and fed a special diet beginning at day 30 supplemented with a particular MO additive daily for up to 126 days. Periodic BW, Scr, BUN and CrCl were measured. A control group of non-nephrectomized rats (n=7, Scr=0.2±0.1) received the same food without any supplement. All of the rats survived (Scr at end=0.5±0.1). Days of survival was the primary endpoint variable. The study ended at day 156.

TABLE 2

| Group | Organism | ALIVE | DEAD | SURVIVE | Mean days | SD | Median |
|---|---|---|---|---|---|---|---|
| G | *S. boulardi* | 2 | 4 | 33.3 | 111 | 44 | 113 |
| B | Placebo | 2 | 4 | 33.3 | 116 | 39 | 122 |
| F | R1001 | 2 | 4 | 33.3 | 116 | 36 | 110 |
| E | SF101 | 3 | 3 | 50 | 126 | 33 | 132 |
| C | *B. pasteruii* | 4 | 2 | 66.7 | 148 | 14 | 156 |
| D | *L. sporogenes* | 5 | 1 | 83.3 | 149 | 16 | 156 |

As shown in Table 2, diets C and D were more effective than G, B, and F ($p<0.05$). Rats fed *L. acidophilus* (NCFM) exhibited a reduction in uremic toxins and showed improved nutritional status with about a ten percent increase in daily caloric intake and 1.6% increase in BMI ($p<0.05$) with no side effects. The study showed that a probiotic containing either or both *B. pasteurii* and *L. sporogenes* is capable of increasing survival in otherwise untreated uremic rats.

EXAMPLE 2

Different formulations were tested on 5/6th nephrectomized mini pigs. From a total of 20 pigs obtained over a six month period, three died post-surgery (one of the three had to be euthanized due to extreme sickness) and two more were euthanized due to acute illness, possibly due to infection.

The mini pigs that were fed formulation 1 were subsequently separated and used again for feeding formulations 2A and 2B. Likewise, 2A was reused for administering formulation 2Ac. A switch was performed using the following procedure. The initial bacterial regimen was stopped and a wash out period of 3 to 4 weeks was allowed prior to a switch to a new treatment regimen. Mini pigs in the other groups were subjected exclusively to the assigned food regimen (3A, 3B, 4A, 5A, respectively). All of the screened, chosen and specially employed probiotic microbial strains are generally recognized as safe (GRAS) classification by FDA except those obtained in the formulations of *B. pastuerii*.

Weight measurement, blood draw and analysis were performed at different time intervals. Due to the small sample size, as well as difference in body weights and the measurement intervals, regression analysis and curve fitting were used to assess the data. Generally, these mathematical techniques are used to explain and/or preduct additional data points. Present analysis determined changes in body weight, BUN, creatinine levels for each mini pig. The details of the formula, number of pigs, delivery mode, daily dosage, duration, composition, and a general summary of the findings are listed in Table 3.

TABLE 3

| Formula (% of pigs) | Delivery mode/ Daily dosage duration (days) | Composition per dose, CFU | Summary of Findings |
|---|---|---|---|
| 1 (6) | Double Layered gelatin capsule/ 1 to 12/ 27 to 30 | *S. thermophilus*, *L. bulgarious*, *L. acidophilus*, *S. bifidos* ($10 \times 10^9$/cap)(1:1:1:1) | BUN decrease Creatinine slight decrease Weight increase |
| 2A (2) | Frozen food ball/ 1 to 2/ 89 | *B. pasteurii* ($6 \times 10^9$), *B. coagulans* ($10 \times 10^9$) | BUN increase Creatinine slight decrease Weight increase |
| 2B (3) | Frozen food ball/ 1 to 2/ 69 | *B. coagulans* ($10 \times 10^9$) | BUN slight decrease Creatinine slight decrease Weight stable |
| 2Ac (2) | Tablet/ 10/ 15 | *B. coagulans* ($0.78 \times 10^8$/tab) | BUN increase Creatinine slight decrease Weight slight decrease |
| 3A (3) | Frozen food balls/ 1 to 4/ 100 | *S. thermophilus* ($11.8 \times 10^9$), *L. acidophilus* ($1 \times 10^9$), *B. longum* ($1 \times 10^9$) | BUN stable Creatinine stable Weight stable |
| 3B (2) | Frozen food balls/ 1 to 4/ 100 | *L. acidophilus* ($1 \times 10^9$), *B. longum* ($1 \times 10^9$) | BUN stable Creatinine stable Weight stable |

TABLE 3-continued

| Formula (% of pigs) | Delivery mode/ Daily dosage duration (days) | Composition per dose, CFU | Summary of Findings |
|---|---|---|---|
| 4A (3) | Frozen food balls/ 1 to 10/ 51 | S. thermophilus $(11.6 \times 10^9)$, L. acidophilus $(1 \times 10^8)$, B. longum $(1 \times 10^9)$ | BUN stable Creatinine slight decrease |
| 5A (2) | Gelatin capsule/ 3 to 10/ 20 (ongoing) | S. thermophilus $(20.4 \times 10^9)$, L. acidophilus $(1 \times 10^9)$, B. longum $(1 \times 10^8)$ | Weight increase BUN decrease Creatinine decrease Weight inconclusive |

Of the several probiotic oral formulations tested, a formulation of four microbial strains (formulation 1) on a low frequency dosage regimen in these 5/6th Nephrectomized Mini pigs (n=6) exhibited (a) continued gain in body weights—approximately 33%, (b) decreased BUN and as well creatinine levels decreased by approximately 13%. In a similar manner two mini pigs on formulation 5A also demonstrated decreased BUN and Creatinine levels, although the body weight of one mini pig increased and that of the other decreased. In addition, the formulation 3A, 3B and 4A demonstrated stable or slight increase in body weights, somewhat stable or slight decreased levels or urea and creatinine levels. In general, all of these data and findings reflect that at least nitrogenous waste metabolites (urea and creatinine) were not accumulating in the blood. These results show that a suitable combination of selectively chosen probiotic microbes are suitable for oral gut-based uremia therapy.

What is claimed is:

1. A composition for improving renal function comprising at least one probiotic bacterium, wherein the probiotic bacterium is a *Streptococcus* selected for converting nitrogenous wastes into non-toxic compounds, wherein said *Streptococcus* is enterically coated, wherein said *Streptococcus* is selected for reducing urea concentrations by exposing the *Streptococcus* to increasing amounts of urea and selecting for bacteria that reduce urea concentrations from 300 mg/dL to 20 mg/dL within 24 hours at pH 6.3.

2. A method for improving renal function in a subject comprising administering to a subject the composition of claim 1 thereby improving renal function in the subject.

* * * * *